United States Patent [19]

Raykovitz

[11] Patent Number: 5,342,861

[45] Date of Patent: Aug. 30, 1994

[54] HOT MELT WETNESS INDICATOR

[75] Inventor: Gary Raykovitz, Flemington, N.J.

[73] Assignee: National Starch and Chemical Investment Holding Corporation, Wilmington, Del.

[21] Appl. No.: 142,628

[22] Filed: Oct. 22, 1993

Related U.S. Application Data

[62] Division of Ser. No. 669,175, Mar. 14, 1991, abandoned.

[51] Int. Cl.$^5$ .................. A61F 13/15; A61F 13/20; C08L 57/10; C08L 51/08
[52] U.S. Cl. .................. 523/111; 428/288; 428/290; 523/118; 604/361
[58] Field of Search .............. 523/111, 118; 604/361; 428/288, 290

[56] References Cited

U.S. PATENT DOCUMENTS

| | | | |
|---|---|---|---|
| 3,731,685 | 5/1973 | Eidus | 128/284 |
| 3,891,584 | 6/1975 | Ray-Chaudhuri et al. | 260/27 R |
| 3,952,746 | 4/1976 | Summers | 128/287 |
| 4,231,370 | 11/1980 | Mroz et al. | 128/287 |
| 4,325,851 | 4/1982 | Colon et al. | 524/63 |
| 4,331,576 | 5/1982 | Colon et al. | 524/271 |
| 4,543,390 | 9/1985 | Tanaka et al. | 525/63 |
| 4,681,576 | 7/1987 | Colon et al. | 604/361 |
| 4,743,238 | 5/1988 | Colon et al. | 604/361 |
| 4,834,733 | 5/1989 | Huntoon et al. | 604/361 |
| 4,895,567 | 1/1990 | Colon et al. | 604/361 |
| 5,035,691 | 7/1991 | Zimmel et al. | 523/111 |
| 5,066,711 | 11/1991 | Colon et al. | 524/272 |
| 5,089,548 | 2/1992 | Zimmel et al. | 523/111 |

OTHER PUBLICATIONS

Stone, F. W., Stratta, J. J., "Ethylene Oxide Polymers", 1967, Reprint from: *Encyclopedia of Polymer Science and Technology*, vol. 6, pp. 103–145, Union Carbide Corporation.

*Primary Examiner*—Peter Szekely
*Attorney, Agent, or Firm*—Ellen T. Dec

[57] ABSTRACT

A wetness indicating hot melt adhesive composition comprising:
  a) a graft copolymer of
    i. about 40–80% by weight of vinyl monomer; and
    ii. about 20–60% by weight of water-soluble polyalkylene oxide polymer having a molecular weight of about 3,000–20,000 and a polymerized ethylene oxide content of at least 50% by weight; and
  b) an effective amount of a wetness indicating agent.

11 Claims, No Drawings

HOT MELT WETNESS INDICATOR

This application is a continuation, division of application Ser. No.07/669,175, filed Mar. 14, 1991, now abandoned.

Hot melt adhesives which are applied to a substrate when molten and cool to harden the adhesive layer are well known in the disposable industry. These adhesives have found widespread use in the construction of disposable baby and adult diapers, sanitary napkins and hospital bed pads. In these constructions, the adhesive is either sprayed onto a substrate or applied in longitudinal, parallel or bead multi-lines or by slot, gravure, screen printing or printed so as to laminate a water resistant covering (e.g., a polyolefin film) which forms the outer shell to tissue or non-woven moisture absorbent substrates. It is often desirable to know from visual observation when the disposable item is wet and thus a hot melt construction adhesive which signals the presence of water by a color change is invaluable.

A variety of approaches have been taken to providing such an adhesive, including that taught in U.S. Pat. No. 4,743,238 issued May 10, 1988 to Colon, et al., wherein the hot melt adhesive is based on a vinyl pyrrolidone based polymer containing an acidic composition. The Colon composition has several deficiencies, and particularly exhibit poor thermal stability. Thus, when heat aged, the adhesives severely degrade as manifested by char, skin formation and color darkening. An additional deficiency is the minimum intensity of the color change of the adhesive when wet. This aspect is especially important since the substrates on which the adhesive is coated are generally opaque. Another deficiency is that due to the high acidic components in the Colon composition products based on this technology are very harsh on applicating equipment (pumps, etc.)

In addition to thermal stability and a rapid response in color change upon exposure to urine, it is also important that adhesives be capable of resisting color change when stored or used under high humidity conditions. Moreover, the adhesives to be used in these applications should be non-irritating, readily-applicable using commercial machinery, possess long open time, and have good adhesion to tissue, non-wovens and plastic substrates.

In accordance with the invention, a superior wetness indicating hot melt adhesive for use in disposable constructions is prepared by the addition of a wetness indicating agent to a water dispersible graft copolymer of a vinyl monomer and polyalkylene oxide, optionally in the presence of a compatible tackifying resin. In a particular embodiment of the invention, a diaper or other disposable non-woven article is provided which contains the wetness indicating hot-melt adhesive composition of the invention.

The vinyl monomers used in preparing the graft copolymers are preferably vinyl acetate and the lower alkyl-substituted acrylates such as methyl acrylate and ethyl acrylate. Other vinyl monomers useful in the present invention include the alkyl esters of acrylic acid containing 1 to 8 carbon atoms in the alkyl portion; styrene; and vinyl esters such as vinyl propionate, vinyl butyrate and the like. Use of the vinyl monomers, and in particular the vinyl acetate monomer, provides sufficient chain transfer in grafting to produce a graft copolymer which is thermally stable, moderately polar and readily formulatable into an adhesive composition.

The water-soluble polyalkylene oxide polymers which are grafted onto the vinyl monomers have a weight average molecular weight of about 3,000 to 20,000 and a polymerized ethylene oxide content of at least 50% by weight. The polyalkylene oxide polymers may be homopolymers of ethylene oxide (including the ester and ether derivatives thereof), random copolymers of ethylene and propylene oxide, block copolymers of ethylene and propylene oxides, or mixtures thereof. It will be noted that mixtures of different polyalkylene oxide polymers may be utilized, and copolymers and homopolymers may be used together in such mixtures. The polymers are commercially available from companies such as Union Carbide (the polyethylene oxide polymers, poly (ethylene oxide/propylene oxide) copolymers and monomethyl ethers of polyethylene oxide), Jefferson (the polyethylene oxide polymers), BASF Wyandotte (the block copolymers) and Dow Chemical Company. More specifically, the Union Carbide products sold under the trade names CARBOWAX ® (for polyethylene oxides) and METHOXY CARBOWAX ® (for the monomethyl ethers of polyethylene oxide) have an average molecular weight roughly indicated by the numeral following the trade name.

The polymerized ethylene oxide content of the polyalkylene oxide polymer should be at least 50% by weight of the polymer and preferably at least 75%. Polymers having a lower content of polymerized ethylene oxide groups display only limited solubility in water, and hence are not useful as the water-sensitive polymer component of the present invention.

The polyalkylene oxide polymers having a molecular weight of less than about 3,000, when used as the sole polyalkylene oxide, have been found not to impart water dispersibility to the graft copolymers, and hence, such lower molecular weight polyalkylene oxide fractions should not be included in determining the proportion of the water-soluble component present in the graft copolymer. On the other hand, such low molecular weight polyalkylene oxides (e.g., CARBOWAX 600 ®) are useful as plasticizers or diluents.

The graft copolymer is preferably formulated with from about 60 to 90% of the vinyl monomer and about 10–45% by weight of the water-soluble polyalkylene oxide polymer, and most preferably containing 25 to 40% by weight of the polyalkylene oxide component.

While various vinyl monomers may be utilized by themselves for grafting onto the water-soluble polymer backbone, small amounts of other ethylenically unsaturated monomers may be utilized as comonomers with the vinyl monomer to improve particular properties such as water-dispersibility, adhesion, softness and the like. Monomers useful as comonomers with the vinyl monomers include 2-hydroxyethyl acrylate, N-vinyl pyrrolidone, sodium vinyl sulfonate (the sodium salt of ethylene sulfonic acid) and the alkyl esters of methacrylic acid containing 1–8 carbon atoms in the alkyl portion. Such comonomers are generally utilized in quantities not exceeding about 10% by weight of the total graft copolymer.

The graft copolymers used herein as well as a process for the production thereof is described in U.S. Pat. No. 3,891,584 issued Jun. 24, 1975 to Ray-Chaudhuri, et al., the disclosure of which is incorporated by reference.

In addition to the water-soluble polyalkylene oxide polymer, vinyl monomer and optional ethylenically unsaturated monomers, the adhesive may also contain one or more compatible tackifying resins in amounts up to about 90% by weight. Such resins primarily produce a reinforcing effect or plasticizing (flexibility) effect, but also contribute stickiness, particular wetting ability, and viscosity control to the graft copolymer. Exemplary of such tackifying resins are rosin (from gum, wood or tall oil) and the rosin derivatives, the phenolic modified coumarone indene resins (sold by Neville Chemical Company of Neville Island, Pa. under the trade name of NEVILLAC®), the coumarone indene resins with softening points of about 5° to 117° C. (sold by the aforementioned Neville Chemical Company under the trade name CUMAR®, the phenolic modified terpene resins (sold by Arizona Chemical Company, Inc. of Elizabeth, N.J. under the NIREZ® trade name). (The softening points of the resins referred to above are Ball and Ring softening points determined using method ASTM E28 -58T.)

The adhesive may also contain small amounts, i.e., up to about 25% by weight, of a compatible plasticizing oil and/or wax diluent. Particularly useful is the Unithox 550®, a modified synthetic wax (melting point of 209° F.) available from Petrolite. Other useful diluents include Benzoflex 352®, a 1,4-cyclohexane dimethanol dibenzante from Velsicol Chemical Corporation and Pycal 94®, a phenyl ether of polyethylene glycol, from Atlas Powder.

In order to produce the wetness indicating hot melt adhesives of the invention, a sufficient amount of wetness indicator is added to the graft copolymer. As the wetness indicating agent, a material which is compatible with the compositions and which is capable of changing the color of the adhesive composition quickly when the adhesive composition is wet compared to the color of the dry adhesive composition, may be used in the present wetness indicating adhesive composition. Acid-base indicators, which change color in response to a change in pH, are preferred, because they change color rapidly, and those providing a change to a bright, vivid color are generally most preferred. Acid-base indicators for use in the present compositions are those which change color at a pH in the range of about 3 to 7, such as Ethyl Red, Bromophenol Blue (made by Eastman Kodak), or Bromocresol Green mixed with Bromophenol Blue; Bromophenol Blue is particularly preferred. Other materials which change color in response to water may be used as the wetness indicating agent, such as dyes which are substantially invisible in the dry composition, but which quickly become a vivid color when wet. An example of such a material is the blue dye, Calcocid® Blue 2G, made by American Cyanamid Corporation. The wetness indicating agent is used in an amount effective to provide the composition with a readily visible color when the composition is wet, and of course, the readily visible color must be easily distinguishable from the color of the dry composition; generally about 0.01 to 0.5 wt. %, preferably 0.05%, of indicator, based on the weight of the composition, is adequate.

The following examples illustrate the production of suitable hot melt wetness indicators as well as the use thereof in a variety of disposable applications. The adhesive product can be applied to a substrate such as polyethylene film in an amount sufficient to cause the file to adhere to another substrate such as tissue, nowwoven or polyethylene. When the disposable article gets wet, the adhesive product turns the appropriate color.

In the examples, all parts are by weight and all temperatures in degree Celsius unless otherwise noted.

EXAMPLE 1

A useful graft copolymer of 30 parts poly (ethylene oxide) and 70 parts vinyl acetate (PEG/VA) was prepared (using a single-charge method) by charging the following ingredients into a one liter flask:

| | |
|---|---|
| Polyglycol E-8000 (Dow Chemical Co.) | 150 g |
| t-butyl peroxyperbenzoate | 0.4 g |

The flask was fitted with a stainless steel stirrer, thermometer, condenser, nitrogen inlet tube and dropping funnel containing 350 g of vinyl acetate. 45 ml of the vinyl acetate was added and the mixture was heated to reflux. 1 ml of a 10% solution of 70% benzoyl peroxide in ethyl acetate was added to initiate the polymerization. The remainder of the vinyl acetate was added over a three hour period. The reaction mixture was heated to 155° to 160° C. and held at this temperature for 15 minutes. 5 g of 4-methyl-2,6-di-t-butylphenol was added and the residual monomer was removed by vacuum distillation. The viscosity of the product was 2,525 cps. at 350° F.

The PEG/VA copolymer was then combined as described in Table I to provide wetness indicating hot melt adhesives which were subjected to the following tests:

TESTING PROCEDURES

For each adhesive, three separate five mil coatings were drawn down with a thermometer onto release paper. The samples were then laminated onto the inside of commercial diapers and the time required for the products to change color exposed to by synthetic urine was noted.

Coatings of each sample were made as above and laminated onto the inside of a commercial diaper and were exposed to the following commercial testing conditions:

| | |
|---|---|
| Condition I | 80° F., 80% relative humidity, 48 hours |
| Condition II | 100° F., 90% relative humidity, 4 hours |

The results of the testing are shown in Table I. "Pass" indicates that the laminations did not change color when exposed to the specific temperature/humidity conditions.

TABLE I

| | 1 | 2 | 3 | 4 | 5 | 6 | 7 | 8 |
|---|---|---|---|---|---|---|---|---|
| 30 PEG/70 VA | 100 | 66.7 | 60 | 56.7 | 56.7 | 40 | 20 | 10 |
| Rosin ester | — | 33.3 | 40.0 | 43.3 | 23.0 | 60 | 80 | 90 |
| Bromophenol blue | 0.05 | 0.05 | 0.01 | 0.05 | 0.05 | 0.05 | 0.05 | 0.05 |
| Unithox 550 | — | — | — | — | 20.0 | — | — | — |
| Response time | <1 min | <1 min | <1 min | <1 min | <1 min | <1 min | <1 min | <1 min |
| Condition I | fails | pass | pass | pass | pass | pass | pass | pass |
| Condition II | pass | pass | pass | pass | pass | pass | pass | pass |

EXAMPLE II

Similar response time and high temperature/humidity resistance results were obtained from a hot melt adhesive formulated with 100 parts of the 30 PEG/70 VA polymer and 0.05 parts Calcocid blue.

EXAMPLE III

Another series of hot melt adhesives was prepared with terpene phenolic tackifying resin and a 25 PEG/75 VA polymer. Similar temperature/humidity testing results were obtained with longer response times, in the area of 10–15 minutes, time ranges which may be commercially acceptable for some applications, especially those disposibles which contain high levels of superabsorbent polymers.

TABLE II

|  | 9 | 10 |
|---|---|---|
| 25 PEG/75 VA | 66.7 | 57.1 |
| Terpene phenolic resin | 33.3 | 42.9 |
| Bromophenol blue | 0.03 | 0.035 |

EXAMPLE IV

The following example illustrates products formulated with terpene phenolic resins so as to have varying response times (3 to 5 minutes) when exposed to synthetic urine.

TABLE III

|  | 11 | 12 | 13 | 14 | 15 | 16 |
|---|---|---|---|---|---|---|
| 30 PEG/70 VA | 90 | 80 | 70 | 60 | 50 | 40 |
| Terpene Phenolic | 10 | 20 | 30 | 40 | 50 | 60 |
| Bromophenol blue | 0.05 | 0.15 | 0.05 | 0.05 | 0.05 | 0.05 |
| Response Time (min.) | <1 | <1 | <1 | 3–5 | 3–5 | 3–5 |
| Condition I | Fail | Fail | Fail | Pass | Pass | Pass |
| Condition II | Pass | Pass | Pass | Pass | Pass | Pass |

While it is noted that these adhesives formulated with terpene phenolic resins and high levels of the graft copolymer (11, 12 and 13) do not pass the extended aging condition of Condition I, these adhesives would, nonetheless, be useful in applications where long term exposure to high humidity is not anticipated.

EXAMPLE V

The following adhesives exhibit a response time of less than one minute, and also resist high temperature, high humidity aging.

|  | 17 | 18 |
|---|---|---|
| 30 PEG/70 VA | 60 | 60 |
| Terpene Phenolic | 20 | 30 |
| Rosin Ester | 20 | 10 |
| Bromophenol blue | 0.05 | 0.05 |
| Condition I | Pass | Pass |
| Condition II | Pass | Pass |

We claim:

1. A disposable absorbent article comprising a moisture absorbent substrate, and a water resistant covering for said absorbent substrate, at least one portion of the inner surface of the water resistant covering coated with a wetness indicating hot melt adhesive composition consisting essentially of:
   a) a graft copolymer of
      i. about 40–80% by weight of vinyl monomer selected from the group consisting of vinyl acetate, methyl acrylate, ethyl acrylate and mixtures thereof; and
      ii. about 20–60% by weight of water soluble polyalkylene oxide polymer having a weight average molecular weight of about 3,000–20,000 and a polymerized ethylene oxide content of at least 50% by weight;
   b) an effective amount of a wetness indicating agent; and
   c) 0–90% by weight of a compatible tackifying resin.

2. The disposable article of claim 1 wherein the article is a diaper.

3. The article of claim 1 wherein polyalkylene oxide polymer in the adhesive is selected from the group consisting of homopolymers of ethylene oxide, random copolymers of ethylene and propylene oxides, block copolymers of ethylene and propylene oxides, and mixtures thereof.

4. The article of claim 1 wherein the graft copolymer in the adhesive comprises 70 to 75% vinyl acetate and 25 to 30% polyethylene oxide.

5. The article of claim 1 wherein the graft copolymer in the adhesive additionally contains up to 10% by weight of reacted ethylenically unsaturated comonomers.

6. The article of claim 1 wherein the adhesive additionally containing up to 90% by weight of a compatible tackifying resin.

7. The article of claim 1 wherein the adhesive additionally containing up to 25% by weight of a wax-like diluent.

8. The article of claim 1 wherein the wetness indicator in the adhesive is present in an amount of 0.01 to 0.5% by weight.

9. The article of claim 1 wherein the wetness indicator in the adhesive is an acid base indication capable of causing the composition to change color in response to the presence of moisture in the composition and within a pH range of 3 to 7.

10. The article of claim 1 wherein the wetness indicator in the adhesive is bromophenol blue.

11. The article of claim 1 wherein the wetness indicator in the adhesive is a material which changes color when wet.

* * * * *